(12) United States Patent
Muchero et al.

(10) Patent No.: US 10,106,807 B2
(45) Date of Patent: Oct. 23, 2018

(54) TRANSCRIPTION FACTOR WHICH REGULATES FLAVONOID, PHENYLPROPANOID, TYROSINE, AND TRYPTOPHAN PATHWAYS

(71) Applicants: UT-Battelle, LLC, Oak Ridge, TN (US); University of Tennessee Research Foundation, Knoxville, TN (US); West Virginia University, Morgantown, WV (US)

(72) Inventors: Wellington Muchero, Oak Ridge, TN (US); Jay Chen, Oak Ridge, TN (US); Lee E. Gunter, Oak Ridge, TN (US); Sara Jawdy, Oak Ridge, TN (US); Gerald A. Tuskan, Oak Ridge, TN (US); Anthony Christian Bryan, Knoxville, TN (US); Stephen Difazio, Morgantown, WV (US); Hao-Bo Guo, Oak Ridge, TN (US)

(73) Assignees: UT-BATTELLE, LLC, Oak Ridge, TN (US); WEST VIRGINIA UNIVERSITY, Morgantown, WV (US)

(*) Notice: Subject to any disclaimer, the term of this patent is extended or adjusted under 35 U.S.C. 154(b) by 0 days.

(21) Appl. No.: 14/720,023

(22) Filed: May 22, 2015

(65) Prior Publication Data
US 2015/0353948 A1 Dec. 10, 2015

Related U.S. Application Data

(60) Provisional application No. 62/008,434, filed on Jun. 5, 2014.

(51) Int. Cl.
  *C12N 15/82* (2006.01)
  *C12Q 1/6895* (2018.01)
  *C12N 9/10* (2006.01)

(52) U.S. Cl.
  CPC ....... *C12N 15/8255* (2013.01); *C12N 9/1092* (2013.01); *C12N 15/8218* (2013.01); *C12N 15/8246* (2013.01); *C12N 15/8251* (2013.01); *C12N 15/8254* (2013.01); *C12Q 1/6895* (2013.01); *C12Q 2600/156* (2013.01)

(58) Field of Classification Search
  CPC .................................................. C12N 15/8255
  See application file for complete search history.

(56) References Cited

U.S. PATENT DOCUMENTS

2011/0296556 A1* 12/2011 Sammons ............. A01N 63/02
                                                                800/298

FOREIGN PATENT DOCUMENTS

WO    WO2012/148275    * 11/2012    ............. C12N 15/82

OTHER PUBLICATIONS

B9GPE8_POPTR entered into UniProtKB/TrEMBL; Mar. 24, 2009.*
Tuskan et al., Science (2006) vol. 313; pp. 1596-1604.*
Klee et al., Molecular and General Genetics (1987) vol. 210; pp. 437-442.*
Chen J., et al., Genomic Science Contractors-Grantees Meeting XIV and USDA-DOE Plant Feedstock Genomics for Bioenergy Meeting, Mar. 6-9, 2016; Abstract 2 pp.*
Slotte T. et al. Nature Gentics (epub Jun. 9, 2013) vol. 45, pp. 831-835.*

* cited by examiner

*Primary Examiner* — Russell Kallis
(74) *Attorney, Agent, or Firm* — Scully Scott Murphy & Presser

(57) ABSTRACT

The invention provides plants having desirable levels of sugar release and/or lignin synthesis. The invention further provides methods of selecting plants with such desirable levels of sugar release and/or lignin synthesis; methods of genetically modifying plants to modulate lignin synthesis, sugar release, and modulating phenylalanine, tyrosine, tryptophan and flavonoid production; and uses of such plants.

3 Claims, 6 Drawing Sheets

Specification includes a Sequence Listing.

TRANSCRIPTION FAILED

TRANSCRIPTION

SEQUENCE LISTING

```
<160> NUMBER OF SEQ ID NOS: 4

<210> SEQ ID NO 1
<211> LENGTH: 2045
<212> TYPE: DNA
<213> ORGANISM: Populus

<400> SEQUENCE: 1
ggacaacgaa cacccaagcc caccaaaaac ccctttaacc aaaccaaacc tcttgaaaaa      60
accacaaact gaacacaact gtgtcgtcct gtagtgtaag agaagagaaa gataggagag     120
aaacagagtg aaagccatgg ctcaagtgag caaaatcagc aatggagcac aaaacaccta     180
cacaacaatc catcttttaa aacccaaat acccaaatct ttgtcttcaa tttcatttag      240
atcacagctc attaaagggt cttcttttgg tttgaagcaa tgtaaaaaaa tgggtagttg     300
caagctaaag gttgaacctt tgaaggtttt agcttcaatt gctacagcag agaagccatc     360
aactgtacct gagatcgttt tgcaacccat caaagatatt tctggtactg ttactttacc     420
gggttccaag tctctgtcaa atcggatact ccttcttgct gctctctctg agggtacgac     480
tgttgttgac aatttgttga atagtgatga tgttcattac atgcttggcg cgctaagaac     540
acttggccta catgtggaag ataataagaa actcaaacaa gcaattgtag aaggatgtgg     600
tggccagttt cctgtgggaa aagaagcaaa tgttgatgtt gaacttttcc ttggaaatgc     660
tggaacagca atgcgtccat tgacagctgc tgtaactgct gcaggtggaa attcaagcta     720
```

| | |
|---|---|
| tatacttgat ggggtgccac gaatgaggga gagaccaatt ggtgatttgg ttattggtct | 780 |
| tcagcagctt ggtgcagatg tttcttgttc tcctacaaac tgcccccctg ttcgcataaa | 840 |
| tgcaaatggg ggccttccag ggggaaaggt taaactctct ggatctataa gtagtcaata | 900 |
| cttgactgct ttgctcatgg cagctccttt agctcttgga gatgtggaaa ttgagatcgt | 960 |
| tgacaaattg atttctgttc catatgttga gatgactctg aagttgatgg agcgctatgg | 1020 |
| agtctttgta gaacacagtg ataactggga tcgtttcttt gttcgaggag gtcaaaagta | 1080 |
| caagtctcct aaaaattctt ttgttgaggg cgatgcttca agtgccagtt acttcctagc | 1140 |
| tggtgcagca atcactggtg ggaccatcac tgtcgaaggt tgtgggatgg atagtttgca | 1200 |
| gggagatgta agtttgcag aggttcttga gaaaatggga gccaaagtta cttggacaaa | 1260 |
| gaacagtgtt actgtcactg gaccgccacg agattcttct ggtcagaaac acttgcgtgc | 1320 |
| tgtcgatgta aacatgaaca aaatgccaga tgttgctatg actctggctg ttgttgcgct | 1380 |
| tttcgctgat ggtcctactg ccataagaga tgtggcaagt tggagagtga agaaacaga | 1440 |
| acggatgatt gctatttgca cagaactaag gaagttggga gcaacagttg aagaaggacc | 1500 |
| agattactgt gtgatcactc cacctgagaa actaaatgtg acagagattg acacttatga | 1560 |
| tgatcacagg atggcaatgg cattctctct tgctgcttgt ggagaagtcc aagtcaccat | 1620 |
| caaggaccct ggttgcactc gaaaaacttt cccagactac tttgaggttc ttgagaggta | 1680 |
| cacaaagcat tgagttgcac tcaaaccatt catccatgtg tactagagag agagagaggt | 1740 |
| tatccattac cattagcaac catgggtagt cctgaatcaa cccaagtttt taatgtatcg | 1800 |
| tggtgtaata tttgattact tatgcaagca ggttgatgct gttattgtac tggagactgg | 1860 |
| tcatatgtga aaggaaaagc cggacttagt tcatttaatt attttttactc tcaagagagc | 1920 |
| gagtgtagtt ctagtcaata attatgaact taaatagttc tatttgtttt tccattaatg | 1980 |
| aatcaatcaa tgaatgcttg aagtgatcaa atcaataaat gttcatattt tctattgttt | 2040 |
| tcgca | 2045 |

<210> SEQ ID NO 2
<211> LENGTH: 518
<212> TYPE: PRT
<213> ORGANISM: Populus

<400> SEQUENCE: 2

```
Met Ala Gln Val Ser Lys Ile Ser Asn Gly Ala Gln Asn Thr Tyr Thr
1               5                   10                  15

Thr Ile His Leu Leu Lys Pro Gln Ile Pro Lys Ser Leu Ser Ser Ile
            20                  25                  30

Ser Phe Arg Ser Gln Leu Ile Lys Gly Ser Ser Phe Gly Leu Lys Gln
        35                  40                  45

Cys Lys Lys Met Gly Ser Cys Lys Leu Lys Val Glu Pro Leu Lys Val
    50                  55                  60

Leu Ala Ser Ile Ala Thr Ala Glu Lys Pro Ser Thr Val Pro Glu Ile
65                  70                  75                  80

Val Leu Gln Pro Ile Lys Asp Ile Ser Gly Thr Val Thr Leu Pro Gly
                85                  90                  95

Ser Lys Ser Leu Ser Asn Arg Ile Leu Leu Leu Ala Ala Leu Ser Glu
            100                 105                 110

Gly Thr Thr Val Val Asp Asn Leu Leu Asn Ser Asp Asp Val His Tyr
        115                 120                 125

Met Leu Gly Ala Leu Arg Thr Leu Gly Leu His Val Glu Asp Asn Lys
```

```
            130                 135                 140
Lys Leu Lys Gln Ala Ile Val Glu Gly Cys Gly Gly Gln Phe Pro Val
145                 150                 155                 160

Gly Lys Glu Ala Asn Val Asp Val Glu Leu Phe Leu Gly Asn Ala Gly
                165                 170                 175

Thr Ala Met Arg Pro Leu Thr Ala Ala Val Thr Ala Ala Gly Gly Asn
            180                 185                 190

Ser Ser Tyr Ile Leu Asp Gly Val Pro Arg Met Arg Glu Arg Pro Ile
            195                 200                 205

Gly Asp Leu Val Ile Gly Leu Gln Gln Leu Gly Ala Asp Val Ser Cys
            210                 215                 220

Ser Pro Thr Asn Cys Pro Pro Val Arg Ile Asn Ala Asn Gly Gly Leu
225                 230                 235                 240

Pro Gly Gly Lys Val Lys Leu Ser Gly Ser Ile Ser Ser Gln Tyr Leu
                245                 250                 255

Thr Ala Leu Leu Met Ala Ala Pro Leu Ala Leu Gly Asp Val Glu Ile
            260                 265                 270

Glu Ile Val Asp Lys Leu Ile Ser Val Pro Tyr Val Glu Met Thr Leu
            275                 280                 285

Lys Leu Met Glu Arg Tyr Gly Val Phe Val Glu His Ser Asp Asn Trp
            290                 295                 300

Asp Arg Phe Phe Val Arg Gly Gly Gln Lys Tyr Lys Ser Pro Lys Asn
305                 310                 315                 320

Ser Phe Val Glu Gly Asp Ala Ser Ser Ala Ser Tyr Phe Leu Ala Gly
                325                 330                 335

Ala Ala Ile Thr Gly Gly Thr Ile Thr Val Glu Gly Cys Gly Met Asp
            340                 345                 350

Ser Leu Gln Gly Asp Val Lys Phe Ala Glu Val Leu Glu Lys Met Gly
            355                 360                 365

Ala Lys Val Thr Trp Thr Lys Asn Ser Val Thr Val Thr Gly Pro Pro
            370                 375                 380

Arg Asp Ser Ser Gly Gln Lys His Leu Arg Ala Val Asp Val Asn Met
385                 390                 395                 400

Asn Lys Met Pro Asp Val Ala Met Thr Leu Ala Val Val Ala Leu Phe
                405                 410                 415

Ala Asp Gly Pro Thr Ala Ile Arg Asp Val Ala Ser Trp Arg Val Lys
            420                 425                 430

Glu Thr Glu Arg Met Ile Ala Ile Cys Thr Glu Leu Arg Lys Leu Gly
            435                 440                 445

Ala Thr Val Glu Glu Gly Pro Asp Tyr Cys Val Ile Thr Pro Pro Glu
450                 455                 460

Lys Leu Asn Val Thr Glu Ile Asp Thr Tyr Asp Asp His Arg Met Ala
465                 470                 475                 480

Met Ala Phe Ser Leu Ala Ala Cys Gly Glu Val Gln Val Thr Ile Lys
                485                 490                 495

Asp Pro Gly Cys Thr Arg Lys Thr Phe Pro Asp Tyr Phe Glu Val Leu
            500                 505                 510

Glu Arg Tyr Thr Lys His
            515

<210> SEQ ID NO 3
<211> LENGTH: 7
<212> TYPE: PRT
<213> ORGANISM: Unknown
```

```
<220> FEATURE:
<223> OTHER INFORMATION: sequence motiff
<220> FEATURE:
<221> NAME/KEY: misc_feature
<222> LOCATION: (5)..(5)
<223> OTHER INFORMATION: Xaa can be any naturally occurring amino acid

<400> SEQUENCE: 3

Met Ala Gln Val Xaa Ser Thr
1               5

<210> SEQ ID NO 4
<211> LENGTH: 4
<212> TYPE: PRT
<213> ORGANISM: Populus

<400> SEQUENCE: 4

Lys Lys Leu Lys
1
```

TRANSCRIPTION FACTOR WHICH REGULATES FLAVONOID, PHENYLPROPANOID, TYROSINE, AND TRYPTOPHAN PATHWAYS

This application claims the benefit of U.S. Provisional Application Ser. No. 62/008,434 filed on Jun. 5, 2014, the Specification of which is hereby incorporated by reference.

STATEMENT REGARDING FEDERALLY SPONSORED RESEARCH OR DEVELOPMENT

This disclosure was made with government support under a research project supported by Contract No. DE-AC05-00OR22725 awarded by the U.S. Department of Energy. The government has certain rights in this disclosure.

BACKGROUND OF THE DISCLOSURE

The shikimate pathway is remarkably conserved across prokaryotes and eukaryotes to the extent that heterologous transformation of genes associated with the pathway has been successful across highly divergent organisms including bacteria, fungi and plants. Being the only source of aromatic amino acid-precursors for the phenylpropanoid, tryptophan, tyrosine and flavonoid pathways, as well as shuttling between 30-50% of all fixed carbon, the shikimate pathway is a crucial source of structural, defense, light harvesting and hormone signaling molecules essential for plant survival. Additionally, since humans and animals cannot synthesize aromatic amino acids, they are dependent on this pathway as the only dietary source of these essential amino acids. As such, the shikimate pathway has been extensively studied across highly divergent taxa for economic, nutritional and medicinal reasons. In plants, one of the most characterized steps in the shikimate pathway is the sixth reaction that is catalyzed by the enzyme 5-enolpyruylshikimate 3-phosphate synthase (EPSP) synthase. This enzyme catalyzes the conversion of shikimate 3-phosphate to 5-enolpyruvylshikimate 3-phosphate and is the target of the herbicide glyphosate. Isoforms of this enzyme derived from some microbes are naturally resistant to glyphosate and have been used extensively in heterologous transformation to create herbicide resistant plants. No other roles have been assigned for EPSPs outside of catalysis in the shikimate pathway.

Production of renewable fuel from lignocellulosic plant biomass is based on extraction of sugars from plant cell wall material. This extraction process is hampered by the presence of lignin in the cell wall. Lignins contribute to plant "recalcitrance", a term referring to the inherent resistance of plant material to release polysaccharides and other desirable biomaterials from an interwoven matrix of desirable and undesirable materials (Lynd L R. et al., Science 251:1318-1323 (1991)). Lignins are difficult to break down by physical, chemical and other methods, and processing plant materials to release sugars from lignins requires extensive thermochemical treatment. In addition, lignin processing creates inhibitory byproducts, such as acetylated compounds, that hamper further extraction and fermentation. Acetyl esters released during treatment of cell wall polymers can inhibit saccharification of biomass. The released acetate is also inhibitory to the organisms used to ferment the sugars into useful byproducts. Overcoming plant recalcitrance to releasing biomaterials bound in the cell wall is therefore an issue of primary importance in the development of biofuel technology.

Lignins, complex interlinking biopolymers derived from hydroxyphenylpropanoids, provide rigidity and structure to plant cell walls for plant growth and transport of water and nutrients, and are significant contributors to plant recalcitrance. Lignins are composed primarily of syringyl (S), guaiacyl (G) and p-hydroxyphenyl (H) monolignol subunits, which are derived from sinapyl, coniferyl and p-coumaryl alcohols, respectively. The subunit ratio and resulting structure of plant lignins varies according to the genotype, environment, tissue type and maturity of the plant and as such, lignins are very heterogeneous and can vary significantly between different plants, within different tissues of a single plant and even within a single plant cell (Simmons B A et al., Curr Opin Plant Biol. 13:313-20 (2010)). This complexity and heterogeneity hinders the development of conversion technology able to process a range of sustainable feedstocks in a cost-effective manner.

Reduction of lignin biosynthesis, and decreases in cell wall recalcitrance, is desirable on one hand for biofuel production. Conversely, increases in cell wall recalcitrance and lignin biosynthesis can be desirable for production of lignin-based products such as carbon fibers. Thus, genetic manipulation of biomass feedstock to modulate lignin biosynthesis and sugar release hold promise both for production of improved, economically sustainable lignocellulosic biofuels (Vermerris W. et al., Crop Science 47(S3):S142-S153 (2007); Fu C. et al., PNAS 108:3803-3808 (2011)), for reducing processing costs for cellulose-based products such as pulp and paper or for enhancing the development of lignin-based polymers.

The genus Populus represents an economically important tree crop that has been targeted for use in diverse applications from the pulp and paper industry, carbon sequestration and as a feedstock in the lignocellulosic biofuel industry (Dinus R J. et al., Crit. Rev. Plant Sci. 20:51-69 (2001)). Recently, a study using wild Populus trichocarpa genotypes collected in the Pacific Northwest region demonstrated high phenotypic variation among the accessions in recalcitrance measured by lignin content and sugar release (Studer M H. et al., PNAS 108:6300-6305 (2011)). This study suggested that sufficient variation occurs in wild germplasm to identify specific genetic determinants of the recalcitrance trait by analysis of naturally-occurring allelic variability.

Quantitative trait loci (QTL) studies have been conducted using interspecific mapping of populations to identify genomic regions associated with cell wall phenotypes linked to recalcitrance (Novaes E. et al., New Phytologist 182:878-890 (2009); Yin T. et al., PLoS one 5:e14021 (2010)). Wegrzyn J L. et al., New Phytologist 188:515-532 (2010) and Muchero et al., BMC Genomics 16:4 (2015) demonstrated the feasibility of using linkage disequilibrium (LD)-based association mapping to validate candidate genes with putative functions in cell wall biosynthesis. The extent of LD decay in P. trichocarpa has been described by Slavov G T. et al., New Phytologist 196(3):713-25 (2012), who reported LD decay to below $r^2$=0.2 within 2 kb in more than half of the genes, within a genomewide average 6-7 kb. Given that the average gene size for P. trichocarpa is 5 kb, these results suggest that QTL fine-mapping and association mapping to within single-gene resolution is possible in P. trichocarpa.

Identification and manipulation of genes regulating cell wall biosynthesis and recalcitrance is critical both for efficient production of cellulosic sugars and ethanol from plant biomass, and for production of improved cellulose-based products, such as paper and pulp.

BRIEF SUMMARY OF THE DISCLOSURE

This disclosure provides plants having preferred levels of lignin synthesis, flavonoid synthesis, tryptophan synthesis, tyrosine synthesis, sugar release, S/G ratio, and resistance to stress and pathogens; methods of selecting plants with preferred levels of lignin synthesis, flavonoid synthesis, tryptophan synthesis, tyrosine synthesis, sugar release, S/G ratio, and resistance to stress and pathogens; methods of genetically modifying plants to modulate lignin synthesis, flavonoid synthesis, tryptophan synthesis, tyrosine synthesis, sugar release, S/G ratio, and resistance to stress and pathogens; and uses of such plants. The inventors have determined that the expression and/or activity of Potri.002G146400, a gene encoding a 5-enolpyruvylshikimate-3-phosphate (EPSP) synthase which functions as a transcriptional regulator of phenylpropanoid, tyrosine, tryptophan and flavonoid synthesis. Gain of function or overexpression of this EPSP-like transcription factor results in the preferential allocation of carbon to biosynthesis of tyrosine and flavonoid-related secondary metabolites. The preferential allocation of carbon to tyrosine and flavonoid production results in reduced lignin content. Loss of function or down-regulation of the EPSP-like transcription factor results in preferential allocation of carbon flow towards tryptophan biosynthesis resulting in reduced lignin, tyrosine and flavonoid biosynthesis. Plants with reduced lignin synthesis, increased S/G ratio, enhanced accessibility to cellulose microfibers and resistance to stress and pathogens, based on modulation of the expression or activity of the Potri.002G146400 gene (SEQ. ID. NO: 1), have divergent uses including pulp and paper production, low-lignin forage crops, nutritional enhancement of food crops based on increased flavonoid content, plant-based production of high value flavonoids with medicinal or therapeutic applications, lignin-based carbon fibers, engineering of pathogen- and drought-resistant strains, and ethanol/biofuel production.

In one embodiment, methods of selecting a plant for a lignin, tyrosine, tryptophan, and flavonoid biosynthesis characteristic are provided. The methods include the steps of (a) obtaining nucleic acids from a candidate plant; (b) identifying an allelic variant of the Potri.002G146400 gene in the nucleic acids; and (c) selecting a plant based on the presence of an allelic variant of the Potri.002G146400 gene in the nucleic acids obtained from the plant. The lignin, tyrosine, tryptophan, and flavonoid biosynthesis characteristic can be high or low expression of an enzyme in the lignin, tyrosine, tryptophan, or flavonoid synthesis pathway.

Another embodiment provides methods to detect the presence of an allelic variant of Potri.002G146400 in a plant. The method involves identifying a plant with high or low lignin, tyrosine, tryptophan, and flavonoid levels, or increased S/G ratios, and determining the sequence of the gene at the Potri.002G146400 locus in said plant.

An allelic variant or homolog of Potri.002G146400 can encode a protein having an amino acid sequence with at least one amino acid alteration or deletion relative to the sequence of the protein encoded by SEQ. ID. NO: 1. The allelic variant or homolog can encode a protein having at least 75%, 80%, 85%, 90%, 95%, 98%, or 100% sequence identity to the sequence of the protein encoded by SEQ. ID. NO: 1. Methods to determine nucleic acid sequences are known in the art and include, for example, polymerase chain reaction and nucleic acid hybridization.

Further disclosed herein are nucleic acid inhibitors of expression of Potri.002G146400, or inhibitors of expression of allelic variants of Potri.002G146400, which can be used to reduce expression of the Potri.002G146400 gene and allelic variants thereof, to reduce lignin biosynthesis. Specific nucleic acid inhibitors include antisense RNA, small interfering RNA, RNAi, microRNA, artificial microRNA, and ribozymes. Also disclosed herein are plants and plant cells genetically modified by introduction of the disclosed inhibitors and expression vectors. Expression of such inhibitors and expression vectors in a plant or plant cell can be used in methods to increase glucose and/or xylose release in a plant or plant cell, to increase or decrease lignin, tyrosine, tryptophan, and flavonoid synthesis, or to increase resistance to environmental stress and pathogens, in such genetically modified plants and plant cells. Further disclosed herein are improved methods of producing biofuel from cellulosic biomass, by using plants with reduced or inhibited expression or activity of the Potri.002G146400 gene in biofuel production processes.

This disclosure further provides expression vectors with a nucleotide sequence of SEQ ID NO: 1, or another allelic variant of Potri.002G146400, operably linked to a regulatory region that is functional in a plant. The regulatory region can be an inducible promoter or a tissue-specific promoter, for example, a xylem-specific promoter. Further provided herein are plants and plant cells genetically modified by introduction of such expression vectors, and methods for increasing lignin, tyrosine, tryptophan, and flavonoid synthesis in a plant or plant cell by expressing such expression vectors in a plant or plant cell of interest.

Additionally disclosed are methods of producing paper and pulp, by using plants with increased expression of the Potri.002G146400 gene in paper or pulp production processes. Further disclosed are pulp and paper products produced by this method, using plants with increased expression of the Potri.002G146400 gene.

DETAILED DESCRIPTION OF THE DISCLOSURE

Figure 1A:
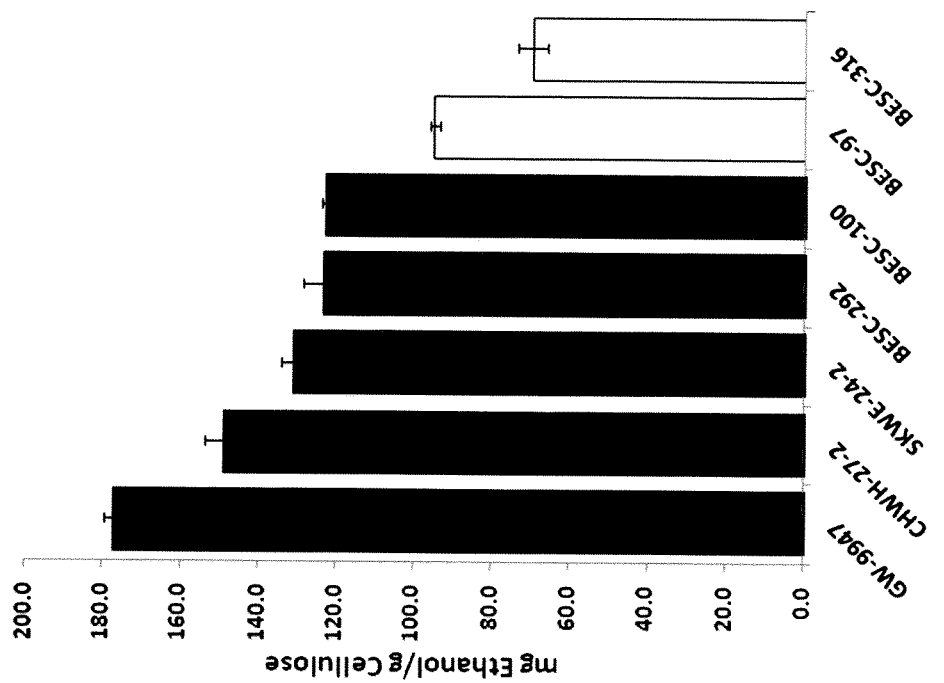
FIG. 1A. Glucose release in *Populus* genotypes carrying loss of function EPSP-like allele (black) compared to *Populus* genotypes carrying the wild-type allele (white).
Figure 1B:
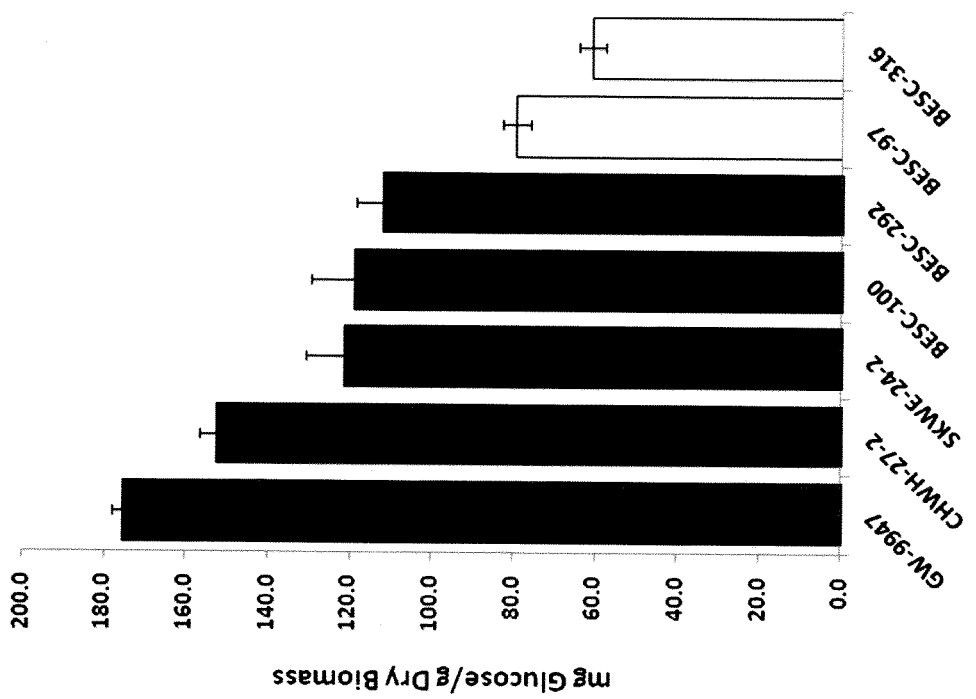
FIG. 1B. Ethanol yield in *Populus* genotypes carrying loss of function EPSP-like allele (black) compared to *Populus* genotypes carrying the wild-type allele (white).

Disclosed herein are plants having desirable levels of lignin synthesis, sugar release, S/G ratio, and resistance to stress and pathogens; methods of selecting plants with preferred levels of lignin synthesis, sugar release, S/G ratio, and resistance to stress and pathogens; methods of genetically modifying plants to modulate lignin synthesis, sugar release, S/G ratio, and resistance to stress and pathogens; and uses of such plants. The inventors have identified a gene, denoted Potri.002G146400, that modulates lignin synthesis, sugar release, S/G ratio, and resistance to stress and pathogens in plants. Potri.002G146400 encodes an EPSP synthase which functions as a transcriptional regulator of phenylpropanoid, tyrosine, tryptophan and flavonoid synthesis. Plants with modulated (increased or decreased) lignin synthesis, sugar release, S/G ratio, and resistance to stress/pathogen characteristics, based on modulation of the expression or activity of the Potri.002G146400 gene, have divergent uses including pulp and paper production, ethanol/biofuel production, and engineering of drought- and pathogen-resistant crops.

The inventors have discovered new naturally occurring alleles in *Populus trichocarpa* associated with cell wall phenotypes. A QTL for lignin biosynthesis and S/G ratio in *P. trichocarpa* was mapped in this study to Potri.002G146400, encoding an EPSP synthase which functions as a transcriptional regulator of phenylpropanoid, tyrosine, tryptophan and flavonoid synthesis. The inventors have determined that altered expression of this gene, either to increase or decrease levels of the functional protein product, leads to a plant with desirable cell wall chemistry suitable for uses including biofuel production, pulp and paper production, forage crop improvement and plant-based synthesis of tyrosine, tryptophan and flavonoids.

The EPSP-like transcription factor is a novel master regulator of secondary cell wall biosynthesis and functions as a transcriptional regulator of phenylpropanoid, tyrosine, tryptophan and flavonoid pathways. The transcription factor modulates the expression of downstream transcription factors including master switches MYB46 and NST1 to regulate the phenylpropanoid, tyrosine, and flavonoid pathways. Gain of function or over-expression of this EPSP-like transcription factor results in the increased expression of MYB46, NST1 transcription factors and PAL and C4H1 genes which are the first and second committed steps in phenylpropanoid/tyrosine biosynthesis. At the same time a key regulator of flavonoid biosynthesis, the COP1-interacting protein 7, is also up-regulated leading to the preferential allocation of carbon to biosynthesis of tyrosine and flavonoid-related secondary metabolites instead of lignin synthesis. Loss of function or down-regulation of the EPSP-like transcription factor results in reduced expression of the PAL and C4H1 genes leading to preferential allocation of carbon flow towards the alternate carbon sink, tryptophan biosynthesis, and reduced lignin, tyrosine and flavonoid biosynthesis.

Characterization of Potri.002G146400 and Sequences

Figure 2A:
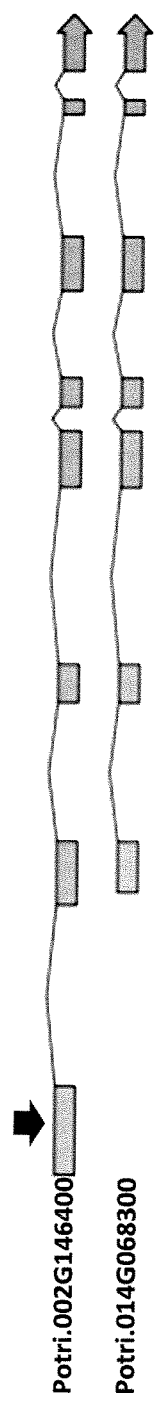
FIG. 2A. Comparison of *Populus* EPSP paralogs showing an additional exon (arrow) encoding an N-terminus helix-turn-helix motif.
Figure 2B:
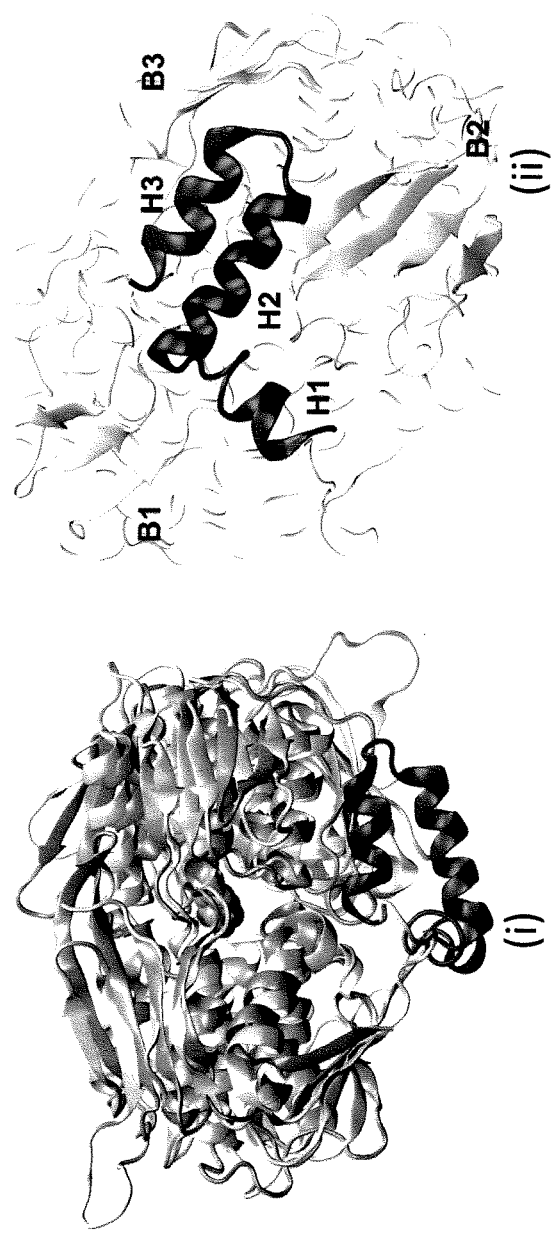
FIG. 2B. *Populus* EPSP synthase (yellow, Potri.002G146400) superimposed on a EPSP synthase from the *Agrobacteria tumefaciens* strain CP4 cystallographic structure (grey, PDB entry 2GG6) bound with a shikimate-3-phosphate substrate (spheres). The HTH domain is indicated by the arrow (FIG. 2A). A detailed view of the HTH domain of the *Populus* EPSP synthase. This domain is comprised of three characteristic α-helixes H1 to H3, which are surrounded by β-sheets B1 to B3 in the enzyme. The rest of the enzyme is shown in ribbons.

The inventors have studied the sequence of Potri.002G146400 gene (SEQ. ID. NO: 1). Potri.002G146400 contains a long N-terminus region that contains as additional 128 amino acids that are not found in paralog Porti.014G068300 (FIG. 2A). Outside this region, the two proteins shared 90.9% sequence identity. Characterization of the tertiary structure arising from the longer N-terminus revealed a putative helix-turn-helix (HTH) motif spanning amino acid resides 30-70 of Potri.002G146400 (FIG. 2B). This motif has three characteristic α-helices surrounded by three β-sheets that are characteristically found in nucleic acid binding HTH domains of transcription factors. The reminder of the protein shares high similarity with the *Agrobacterium tumefaciens*-derived cp4 EPSP synthase (FIG. 2B).

SEQ. ID. NO: 1
(nucleic acid sequence of Potri.002G146400)
GGACAACGAACACCCAAGCCCACCAAAAACCCCTTTAACCAAACCAAACC

TCTTGAAAAAACCACAAACTGAACACAACTGTGTCGTCCTGTAGTGTAAG

AGAAGAGAAAGATAGGAGAGAAACAGAGTGAAAGCCATGGCTCAAGTGAG

CAAAATCAGCAATGGAGCACAAAACACCTACACAACAATCCATCTTTTAA

AACCCCAAATACCCAAATCTTTGTCTTCAATTTCATTTAGATCACAGCTC

ATTAAAGGGTCTTCTTTTGGTTTGAAGCAATGTAAAAAAATGGGTAGTTG

CAAGCTAAAGGTTGAACCTTTGAAGGTTTTAGCTTCAATTGCTACAGCAG

AGAAGCCATCAACTGTACCTGAGATCGTTTTGCAACCCATCAAAGATATT

TCTGGTACTGTTACTTTACCGGGTTCCAAGTCTCTGTCAAATCGGATACT

CCTTCTTGCTGCTCTCTCTGAGGGTACGACTGTTGTTGACAATTTGTTGA

ATAGTGATGATGTTCATTACATGCTTGGCGCGCTAAGAACACTTGGCCTA

CATGTGGAAGATAATAAGAAACTCAAACAAGCAATTGTAGAAGGATGTGG

TGGCCAGTTTCCTGTGGGAAAAGAAGCAAATGTTGATGTTGAACTTTTCC

TTGGAAATGCTGGAACAGCAATGCGTCCATTGACAGCTGCTGTAACTGCT

GCAGGTGGAAATTCAAGCTATATACTTGATGGGGTGCCACGAATGAGGGA

GAGACCAATTGGTGATTTGGTTATTGGTCTTCAGCAGCTTGGTGCAGATG

TTTCTTGTTCTCCTACAAACTGCCCCCCTGTTCGCATAAATGCAAATGGG

GGCCTTCCAGGGGGAAAGGTTAAACTCTCTGGATCTATAAGTAGTCAATA

CTTGACTGCTTTGCTCATGGCAGCTCCTTTAGCTCTTGGAGATGTGGAAA

TTGAGATCGTTGACAAATTGATTTCTGTTCCATATGTTGAGATGACTCTG

AAGTTGATGGAGCGCTATGGAGTCTTTGTAGAACACAGTGATAACTGGGA

TCGTTTCTTTGTTCGAGGAGGTCAAAAGTACAAGTCTCCTAAAAATTCTT

TTGTTGAGGGCGATGCTTCAAGTGCCAGTTACTTCCTAGCTGGTGCAGCA

ATCACTGGTGGGACCATCACTGTCGAAGGTTGTGGGATGGATAGTTTGCA

GGGAGATGTAAAGTTTGCAGAGGTTCTTGAGAAAATGGGAGCCAAAGTTA

CTTGGACAAAGAACAGTGTTACTGTCACTGGACCGCCACGAGATTCTTCT

GGTCAGAAACACTTGCGTGCTGTCGATGTAAACATGAACAAAATGCCAGA

TGTTGCTATGACTCTGGCTGTTGTTGCGCTTTTCGCTGATGGTCCTACTG

CCATAAGAGATGTGGCAAGTTGGAGAGTGAAAGAAACAGAACGGATGATT

-continued
GCTATTTGCACAGAACTAAGGAAGTTGGGAGCAACAGTTGAAGAAGGACC

AGATTACTGTGTGATCACTCCACCTGAGAAACTAAATGTGACAGAGATTG

ACACTTATGATGATCACAGGATGGCAATGGCATTCTCTCTTGCTGCTTGT

GGAGAAGTCCAAGTCACCATCAAGGACCCTGGTTGCACTCGAAAAACTTT

CCCAGACTACTTTGAGGTTCTTGAGAGGTACACAAAGCATTGAGTTGCAC

TCAAACCATTCATCCATGTGTACTAGAGAGAGAGAGAGGTTATCCATTAC

CATTAGCAACCATGGGTAGTCCTGAATCAACCCAAGTTTTTAATGTATCG

TGGTGTAATATTTGATTACTTATGCAAGCAGGTTGATGCTGTTATTGTAC

TGGAGACTGGTCATATGTGAAAGGAAAAGCCGGACTTAGTTCATTTAATT

ATTTTTACTCTCAAGAGAGCGAGTGTAGTTCTAGTCAATAATTATGAACT

TAAATAGTTCTATTTGTTTTTCCATTAATGAATCAATCAATGAATGCTTG

AAGTGATCAAATCAATAAATGTTCATATTTTCTATTGTTTTCGCA

SEQ. ID. NO: 2
(amino acid sequence of Potri.002G146400)
MAQVSKISNGAQNTYTTIHLLKPQIPKSLSSISFRSQLIKGSSFGLKQCK

KMGSCKLKVEPLKVLASIATAEKPSTVPEIVLQPIKDISGTVTLPGSKSL

SNRILLLAALSEGTTVVDNLLNSDDVHYMLGALRTLGLHVEDNKKLKQAI

VEGCGGQFPVGKEANVDVELFLGNAGTAMRPLTAAVTAAGGNSSYILDGV

PRMRERPIGDLVIGLQQLGADVSCSPTNCPPVRINANGGLPGGKVKLSGS

ISSQYLTALLMAAPLALGDVEIEIVDKLISVPYVEMTLKLMERYGVFVEH

SDNWDRFFVRGGQKYKSPKNSFVEGDASSASYFLAGAAITGGTITVEGCG

MDSLQGDVKFAEVLEKMGAKVTWTKNSVTVTGPPRDSSGQKHLRAVDVNM

NKMPDVAMTLAVVALFADGPTAIRDVASWRVKETERMIAICTELRKLGAT

VEEGPDYCVITPPEKLNVTEIDTYDDHRMAMAFSLAACGEVQVTIKDPGC

TRKTFPDYFEVLERYTKH

Allelic Variants and Homologs of Potri.002G146400

As used herein, "allelic variants" are alternative forms of the same gene or genetic locus. Each allelic variant has a distinct nucleic acid sequence at the locus of interest. An allelic variant of the Potri.002G146400 gene can have at least one nucleic acid alteration or deletion relative to the sequence of SEQ ID NO: 1, and can encode a polypeptide that differs by one or more amino acids from SEQ ID NO: 2. Allelic variants can encode different proteins when the difference in nucleic acid sequence results in at least one alteration or deletion in the amino acid sequence between the variants. The allelic variant can encode a polypeptide with a different number of glutamine repeats relative to the sequence of SEQ ID NO: 2.

An allelic variant of Potri.002G146400 can encode the amino acid sequence as set forth in SEQ ID NO: 2, or an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO: 2. Sequence identity refers to the percent of exact matches between the amino acids of two sequences which are being compared. Where one allelic variant encodes a truncated protein relative to the protein encoded by another allelic variant, percent identity can be determined by comparing the amino acid sequences of the variants along the length of the shorter protein.

This disclosure also provides homologs of the polypeptide encoded by Potri.002G146400. A Potri.002G146400 homolog can be a homolog, ortholog or variant of the polypeptide having the amino acid sequence set forth in SEQ ID NO: 2. For example, a Potri.002G146400 homolog can have an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO: 2.

In some embodiments, a homolog of Potri.002G146400 is a functional homolog. A functional homolog is a polypeptide that has sequence similarity to SEQ ID NO: 2 and that carries out one or more of the biochemical or physiological function(s) of the polypeptide of SEQ ID NO: 2. A functional homolog may be a natural occurring polypeptide and the sequence similarity may be due to convergent or divergent evolutionary events. As such, functional homologs are sometimes designated in the literature as homologs or orthologs or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cell wall-modulating polypeptide or by combining domains from the coding sequences for different naturally-occurring cell wall-modulating polypeptides ("domain swapping"). The term "functional homolog" can also be applied to the nucleic acid that encodes a functionally homologous polypeptide.

A homolog of Potri.002G146400 can be a native Potri.002G146400 protein, i.e., one or more additional copies of the coding sequence for a Potri.002G146400 homolog that is naturally present in the cell. Alternatively, a homolog of Potri.002G146400 can be heterologous to the cell, e.g., a transgenic *Populus* plant can contain the coding sequence for a Potri.002G146400 homolog from an *Arabidopsis* plant, for example. Potri.002G146400 homologs from multiple species are identified in FIGS. 3A-3H.

Allelic Variation and Modulation of the Potri.002G146400 Gene is Associated with Altered Lignin, Tyrosine, Tryptophan and Flavonoid Synthesis, Sugar Release, S/G Ratio, and Resistance to Environmental Stress and Pathogens This disclosure further provides for modulation of the Potri.002G146400 gene. "Modulation" refers to changing the expression or activity of the Potri.002G146400 gene.

One specific form of modulation is altering start codon usage to eliminate the n-terminus helix-turn-helix motif. Use of the start position at position 129 of the amino acid sequence results in ancestral isoform of the EPSP gene which lack transcriptional regulatory activity. Further, mutation of the nuclear localization signal KKLK at positions 144-147 of the amino acid sequence results in loss of transcriptional activity.

The Potri.002G146400 gene can also be modulated by increasing or decreasing expression of the gene itself. Methods to modulate expression are disclosed in detail below.

Allelic variation and modulation of the Potri.002G146400 gene can lead to proteins with altered activity. "Altered activity" includes an increase or decrease in a known activity of a protein encoded by a gene of interest, including loss of an established or proposed function, or gain of a new function. For example, the inventors have discovered that plants harboring the Potri.002G146400 gene have low lignin biosynthesis. As the Potri.002G146400 gene encodes an ESPS synthase, activities that can be altered for this gene include, but are not limited to, DNA binding, activation of one or more downstream genes, and binding to one or more co-factors.

The inventors have determined that allelic variants of the Potri.002G146400 gene have altered S/G ratios, distinctive sugar release characteristics, and distinctive lignin synthesis characteristics, that produce plants with desirable qualities. The inventors have further determined that manipulating the Potri.002G146400 gene, for example, by manipulating the expression of the Potri.002G146400 gene or by increasing or decreasing the number of glutamine repeats in the protein, can modulate S/G ratio, sugar release, and/or lignin content.

Altered S/G ratios in a plant (e.g., *Populus* species) include, for example, alterations from essentially 50% syringyl ("S"):50% guaiacyl ("G") units to essentially 100% syringyl units, or essentially 100% guaiacyl units. The terms "units" and "subunits" are used interchangeably herein. Specific S/G ratios include, for example, greater than 2:1, e.g., 2.1:1, 2.2:1, 2.5:1, 2.8:1, 3.0:1, 3.5:1, 4:1, etc; or less than 2:1, e.g., 0.5:1, 0.8:1, 1:1, 1.2:1, 1.5:1, 1.8:1, etc. The ratio of syringyl to guaiacyl units can be increased or decreased, e.g., by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a plant as compared to the corresponding S/G ratio in a control plant (i.e., without the manipulation of the Potri.002G146400 gene). In some cases, the ratio of syringyl units incorporated into lignin in a plant described herein can be increased or decreased, e.g., by 5%, 10%, 15%, 20%, 25%, 30%, 35%, 40%, 45%, 50%, 60%, 70%, 80%, 90%, 100% or more than 100%, as compared to the corresponding ratio in a control plant.

By manipulating the Potri.002G146400 gene, the amount and/or rate of S subunit to G subunit biosynthesis, or the incorporation of S to G subunits into the lignin structure, can be altered. Alteration in the S/G subunit ratio alters the lignin composition of the plant cell wall. Manipulating the Potri.002G146400 gene can thus modulate the lignin composition of a plant.

G units have greater capacity for cross-linking between monomers relative to S units. Thus, increasing the ratio of S/G subunits to greater than 2:1 increases S subunits and decreases G subunits in lignin and thus decreases cross-linking between subunits incorporated into lignin. This makes plants with an S/G ratio greater than 2:1 more degradable than wild-type plants because there is less cross-linkage between lignin units and therefore plants with an S/G ratio greater than 2:1 are more susceptible to extraction processes, which decreases recalcitrance and increases sugar release. Higher S/G ratio has been shown to increase sugar release in *Populus* at values above 2.0. The exact way this occurs is not known though it is speculated that lignin remains intact during saccharification under high temperature and/or pressure. Nevertheless, biomass with an S/G ratio above 2.0 releases more sugar.

"Sugar release" includes high or low release of sugars, also referred to as low or high recalcitrance. "High" sugar release (i.e., low recalcitrance) means that sugar can be extracted more easily, or more sugar can be extracted, from a plant, under conditions that would result in less sugar release in a plant without the particular allelic variant. "Low" sugar release (i.e., high recalcitrance) means that sugar can be extracted less easily, or less sugar can be extracted, from a plant, under conditions that would result in more sugar release in a plant without the particular allelic variant. In one example, sugar release refers to the amount of 5- and 6-carbon sugars that can be recovered from a plant using standard techniques to extract these sugars from plant materials. Sugars that can be released include, but are not limited to, glucose, xylose, fructose, arabinose, lactose, ribose, mannose, galactose, and sucrose. Examples of 5-carbon sugars (pentoses) include xylose, ribose, and arabinose; examples of 6-carbon sugars include glucose, fructose, mannose, and galactose.

Sugar release can be measured, for example, by saccharification analysis. In one example of saccharification analysis, sugars are extracted with alpha-amylase and β-glucosidase in sodium acetate, followed by an ethanol soxhlet extraction. After drying overnight, water is added, and samples are sealed and reacted. Once cooled, a buffer-enzyme mix with cellulose oxidative enzymes is added and incubated with the sample. After incubation, an aliquot of the saccharified hydrolysate is tested for sugar content/release, such as by addition of glucose oxidase/peroxidase for measuring glucose content, and/or xylose dehydrogenase to measure xylose content.

High or low sugar release can be an increase or decrease in sugar release or sugar recovery of 2%, 5%, 8%, 10%, 15%, 20%, 25%, 30%, 40%, 50%, 60%, 70%, 80%, 90%, or 100% in a plant with a particular Potri.002G146400 allelic variant, relative to sugar release or sugar recovery from a plant that does not have the Potri.002G146400 allelic variant. In one example, "low" glucose release is glucose release of less than 0.1, 0.15, 0.2, or 0.25 g glucose per g biomass. "High" glucose release is glucose release of 0.3, 0.35, 0.4, or 0.45 g glucose per g biomass or more. "Low" glucose/xylose release is combined release of glucose and xylose of less than 0.2, 0.25, 0.3, 0.35, or 0.4 g combined glucose/xylose per g biomass. "High" glucose/xylose release is combined release of glucose and xylose above 0.4, 0.45, 0.5, 0.55, or 0.6 g combined glucose/xylose per g biomass.

"Lignin" is a complex polymer composed of monolignol subunits, primarily syringyl (S), guaiacyl (G) and p-hydroxyphenyl (H) monolignols, derived from sinapyl, coniferyl and p-coumaryl alcohols, respectively. Differences in the ratio of monolignols, and differences in expression and/or activity of lignin biosynthetic anabolic enzymes, create considerable variability in lignin structures, which differ between species, within species, within different tissues of a single plant and even within a single plant cell.

Lignin "synthesis" or "biosynthesis" refers to the production of lignin in a plant, plant tissue, or plant cell. "Lignin synthesis characteristics" or "lignin biosynthesis characteristics" include the total amount of lignin ("lignin content") in a plant or plant cell, the ratio or amount of monolignol subunits, and expression and/or activity of lignin biosynthetic enzymes. Lignin content, ratio or amount of monolignols, and expression and/or activity of lignin biosynthetic enzymes, can be affected by allelic variation in the Potri.002G146400 gene, where one or more of these characteristics can be high or low relative to the same characteristic or characteristics in a plant that does not have the same Potri.002G146400 allelic variant.

Enzymes in the lignin synthesis pathway that can show high expression, high activity, low expression, or low activity, depending on the allelic variant of Potri.002G146400 present in the plant, include, but are not limited to, phenylalanine ammonia lyase (PAL), cinnamate 4-hydroxylase (C4H), 4-coumarate coenzyme A ligase (4CL), ferulate 5-hydroxylase (F5H), p-coumarate 3-hydroxylase (C3H), p-hydroxycinnamoyl-Co A:quinate/shikimate hydroxycinnamoyl transferase (HCT), caffeoyl-CoA O-methyltransferase (CCoAOMT), cinnamoyl-CoA reductase (CCR), caffeic acid O-methyltransferase (COMT), and cinnamyl alcohol dehydrogenase (CAD).

Lignin forms strong bonds with sugars and interferes with access to these carbohydrates, making it difficult to extract the plant's sugars contained in cellulose and hemicellulose. Differences in lignin content alter the sugar release properties of a plant in the extraction process. Lower lignin levels in a plant are associated with higher levels of sugar release, while higher lignin levels are associated with lower levels of sugar release. Thus, sugar release and lignin content can show an inverse correlation.

Variants of Potri.002G146400, particularly variants with increased glutamine repeats relative to the number of glutamine repeats in SEQ ID NO: 2, have improved resistance to stress, specifically environmental stress, and pathogens. Environmental stresses include dehydration/drought, lack of sunlight, lack of nutrients, poor soil conditions, elevated temperatures, etc. Pathogens include, but are not limited to, single stranded RNA viruses (with and without envelope), double stranded RNA viruses, and single and double stranded DNA viruses such as (but not limited to) tobacco mosaic virus, cucumber mosaic virus, turnip mosaic virus, turnip vein clearing virus, oilseed rape mosaic virus, tobacco rattle virus, pea enation mosaic virus, barley stripe mosaic virus, potato viruses X and Y, carnation latent virus, beet yellows virus, maize chlorotic virus, tobacco necrosis virus, turnip yellow mosaic virus, tomato bushy stunt virus, southern bean mosaic virus, barley yellow dwarf virus, tomato spotted wilt virus, lettuce necrotic yellows virus, wound tumor virus, maize steak virus, and cauliflower mosaic virus. Other pathogens within the scope of the invention include, but are not limited to, fungi such as *Cochliobolus carbonum, Phytophthora infestans, Phytophthora sojae, Collesosichum, Melampsora lini, cladosporium fulvum, Hemint-hosporium maydia, Peronospora parasitica, Puccinia sorghi,* and *Puccinia polysora*; bacteria such as *Phynchosporium secalis, Pseudomonas glycinea, Xanthomonas oryzae* and *Fusarium oxyaporium*; and nematodes such as *Globodera rostochiensis.*

Measuring Lignin Synthesis

Methods to determine if a plant has altered lignin synthesis include, for example, directly measuring lignin content, or by determining the expression or activity of genes in the lignin biosynthetic pathway. Lignin content can be measured directly, for example, by thioglycolysis, or by histochemical analysis of tissue sections stained with toluidine blue O (TBO), Wiesner reagent, or Maiule reagent to identify lignified or non-lignified cell walls. Liginin may also be measured by pyrolysis vapor analysis using pyrolysis Molecular Beam Mass Spectrometry (py-MBMS) (Evans R J. et al., *Energy and Fuels* 1:123-137 (1987); Sykes R. et al., *Biofuels: Methods and Protocols* 169-183 (2009); Tuskan G. et al., *Appl.Biochem. Biotechnol.* 77:55-65 (1999)). Additional methods of measuring carbohydrate and lignin content in biomass are known in the art; see, for example, Sluiter A. et al., Determination of structural carbohydrates and lignin in biomass—laboratory analytical procedure. Technical Report NREL/TP-510-42618:1-17 (2008), available from the National Renewable Energy Laboratory.

Levels of lignin content, or levels of a monolignol (e.g., levels of syringyl, guaiacyl, or p-hydroxyphenyl monolignols), in a plant having an allelic variant of Potri.002G146400 can be higher or lower, e.g., by 5%, 10%, 15%, 20%, 25%, 30%, 35%, 40%, 45%, 50%, 60%, 70%, 80%, 90%, 100% or more than 100%, as compared to the corresponding levels of lignin synthesis or monolignol content in a plant without the same Potri.002G146400 allelic variant. In one example, lignin content is determined by py-MBMS. In this example, "low" lignin content can be less than 5%, less than 10%, less than 15%, less than 20%, or less than 25%. "High" lignin content can be greater than 20%, greater than 25%, greater than 27%, or greater than 30%.

In a preferred embodiment, lignin synthesis is measured by measuring expression and/or activity of lignin biosynthetic enzymes. Lignin biosynthetic enzymes include phenylalanine ammonia lyase (PAL), cinnamate 4-hydroxylase (C4H), 4-coumarate coenzyme A ligase (4CL), ferulate 5-hydroxylase (F5H),p-coumarate 3-hydroxylase (C3H), p-hydroxycinnamoyl-CoA:quinate/shikimate hydroxycinnamoyl transferase (HCT), caffeoyl-CoA O-methyltransferase (CCoAOMT), cinnamoyl-CoA reductase (CCR), caffeic acid O-methyltransferase (COMT), and cinnamyl alcohol dehydrogenase (CAD) (for review, see Wang, et al., *Frontiers Plant Sci.* Vol. 4, Art. 220, pages 1-14 (2013)).

Expression and/or activity of lignin biosynthetic enzymes can be determined by isolating enzymes or lignin content in from plants in vivo. Determinations of expression of lignin synthesis enzymes can also be made in vitro in plants, for example, using protoplast (isolated cell wall-free plant cells) assays. Protoplasts can be propagated from a desired plant using the methods of Guo J. et al., (*PLoS ONE* 7:e44908 (2012)). Briefly, protoplasts are isolated from the plant, and RNA is extracted and subjected to PCR analysis using primers specific for the gene or genes of interest. The expression of a normalization gene, such as a ubiquitin gene, can be used to standardize the expression of each gene. Expression of an enzyme can be compared between protoplasts transfected with an allelic variant of Potri.002G146400 and protoplasts not having the same allelic variant (e.g., protoplasts transfected with a different allelic variant, or without a Potri.002G146400 gene). In one example, the expression of three genes that encode enzymes of three major cell wall components, namely, PtrCesA8 for cellulose biosynthesis, PtrGT43B for hemicellulose biosynthesis and PtrCcoAOMT1 for lignin biosynthesis, can be used to determine expression of cell wallsynthesis enzymes, which correlates with cell wall polymer composition in total.

Methods to Select Plants for Lignin Synthesis, Sugar Release, S/G Ratio, and Resistance to Environmental Stress and Pathogens In one embodiment, methods of selecting a plant for lignin synthesis, sugar release, S/G ratio, and resistance to stress/pathogen characteristics are provided. The methods include the steps of (a) obtaining nucleic acids from a candidate plant; (b) identifying an allelic variant of the Potri.002G146400 gene in the nucleic acids; and (c) selecting a plant based on the presence of an allelic variant of the Potri.002G146400 gene in the nucleic acids obtained from the plant.

The first step in selecting a plant for a lignin synthesis, sugar release, S/G ratio, or resistance to stress/pathogen characteristic is to obtain nucleic acids from a candidate plant. The candidate plant is a plant that may harbor an allelic variant of Potri.002G146400, or a plant that may have altered activity of Potri.002G146400 gene. Methods of obtaining nucleic acids from a candidate plant and detecting the presence of a nucleotide sequence are known in the art. Nucleic acid can be isolated from a plant tissue sample, according to standard methodologies (Sambrook et al., Molecular Cloning, 2nd ed., Cold Spring Harbor Laboratory Press, CSH, 1.38-1.39, 1989).

Detection of Nucleic Acid Sequences

Once nucleic acids are obtained, the next step in selecting a plant having altered lignin synthesis is to detect the presence of an allelic variant of Potri.002G146400 in the candidate plant. Detecting the presence of a target gene, such as an allelic variant of Potri.002G146400, can be accomplished by, for example, hybridization of probes to the target sequence (nucleic acid hybridization), or by amplification of target nucleic acid sequences, followed by detection of target sequences.

A number of template dependent processes are available to amplify the marker sequences present in a given nucleic acid sample. One of the best known amplification methods is the polymerase chain reaction (referred to as PCR). Other methods of amplification are ligase chain reaction (LCR), Qbeta Replicase, isothermal amplification, strand displacement amplification (SDA), PCR-like template- and enzyme-dependent synthesis using primers with a capture or detector moiety, transcription-based amplification systems (TAS), cyclical synthesis of single-stranded and double-stranded DNA, "RACE", one-sided PCR, and di-oligonucleotide amplification.

The PCR method is well known in the art and disclosed, for example, in WO 99/28500; Sambrook et al. (Molecular Cloning—A Laboratory Manual, Cold Spring Harbor Laboratory, Cold Spring Harbor, N.Y. 1989); Nucleic Acid Hybridization (Hames and Higgins eds., 1984); and Current Protocols in Human Genetics (Dracopoli et al., eds, 1984 with quarterly updates, John Wiley & Sons, Inc.), all of which are incorporated herein by reference. The PCR method utilizes a pair of oligonucleotide primers, each hybridizing to one strand of a double-stranded DNA/RNA target. The primers flank the region that will be amplified. The PCR method comprises contacting the primers and target sequence, or mixture of target sequences and optional polynucleotide probes, and performing the amplification steps.

Allelic variants can be detected by hybridization of nucleic acid probes to the target sequence. As used herein, a "probe" is an oligonucleotide that is capable of hybridizing to a target nucleic acid sequence, and which also has additional features (e.g., a fluorescent moiety, a dye, a bead, a particle, a nucleic acid sequence, etc) which allow for detection, immobilization, or manipulation of the target nucleic acid sequence. A "probe set" or "probeset" is a collection of two, three, or more probes designed to interrogate a given sequence. In contrast, a "primer" is an oligonucleotide that is capable of hybridizing to a target nucleic acid sequence and serves as a starting point for DNA synthesis/amplification. Primers may or may not contain additional features for detection, immobilization, or manipulation of the target nucleic acid sequence. For both probes and primers, the hybridizing portion is a stretch of preferably 10-50, more preferably 15-35, and most preferably 15-30 nucleotides. Suitable probes and primers (e.g., DNA probes and primers, RNA probes and primers) for hybridization to a target nucleic acid include, but are not limited to, probes and primers having at least about 70%, 75%, 80%, 85%, 90%, 95%, 98% or 99% complementarity to a target nucleic acid sequence, as well as probes and primers that have complete complementarity to a target nucleic acid sequence. Methods for preparation of labeled DNA and RNA probes and primers, and the conditions for hybridization thereof to target nucleic acid sequence, are described in Molecular Cloning: A Laboratory Manual, J. Sambrook et al., eds., 2nd edition (Cold Spring Harbor Laboratory Press, 1989), Chapters 10 and 11, the disclosures of which are incorporated herein by reference.

Primers for nucleic acid amplification of the Potri.002G146400 gene should contain a hybridizing region exactly or substantially complementary or corresponding to a target nucleotide sequence. Primer extension is performed under hybridization conditions of sufficient stringency to allow the selective amplification of the target sequence. A primer can either consist entirely of the hybridizing region or can contain additional features which allow for detection, immobilization, or manipulation of the amplified product, but which do not alter the basic property of the primer (that is, acting as a point of initiation of DNA synthesis).

Once an allelic variant of the Potri.002G146400 gene, is identified in a candidate plant, the plant is selected as a plant having particular lignin synthesis, sugar release, S/G ratio, or stress/pathogen resistance characteristic. Sugar release characteristics include high or low sugar release, such as high or low release of glucose and/or xylose. Preferred sugar release characteristics include high release of glucose and/or xylose. Lignin synthesis characteristics include high or low expression of at least one enzyme in the lignin synthesis pathway, and low lignin content. S/G ratio characteristics include increased or decreased S/G ratios. Stress resistance characteristics include increased resistance to dehydration/drought, lack of sunlight, lack of nutrients, poor soil conditions, and elevated temperatures. Pathogen resistance characteristics include increased resistance to one or more plant pathogens, particularly viral or bacterial plant pathogens.

In one example, the allelic variant encodes the polypeptide of SEQ ID NO: 2. In another example, the allelic variant is SEQ ID NO: 1. In a further example, the allelic variant can encode at least one amino acid alteration (substitution of one amino acid for another), addition, or deletion (removal of an amino acid) relative to the amino acid sequence of SEQ ID NO: 2.

Overexpression of the EPSP-like transcription factor results in increased accumulation of secondary metabolites including but not limited to flavonoids. The compounds possess potent anti-oxidant activities that have been linked to preservation of cellular integrity during oxidative stress and/or aging. Additionally, flavonoids such as quercetin have been described to have anti-cancer activities (Avila et al., 1994) while dihyromyricetin has been shown to have both anti-cancer and anti-alcohol intoxication properties (Shen et al., 2012). Increased flavonoid production is also desirable for enhanced nutritional quality in fruits and vegetables as well as for aesthetics in ornamental plants and flowers.

Selection and Screening Using the Potri.002G146400 Gene

The sequence of an allelic variant of the Potri.002G146400 gene can be used as a molecular marker for use in screening germplasm in plant breeding programs. Primers targeting conserved regions of the gene can be used to identify genotypes carrying alterations that lead to amino acid substitutions which can affect gene function. A population of plants can be screened or selected for those members of the population that have a desired trait or phenotype. Selection or screening can be carried out over one or more generations, which can be useful to identify those plants that have a desired characteristic, such as low recalcitrance, low lignin synthesis, high S/G ratio, and/or increased stress or pathogen resistance. Selection or screening can be carried out in more than one geographic location. In some cases, transgenic plants can be grown and selected under conditions which induce a desired phenotype or are otherwise necessary to produce a desired phenotype in a transgenic plant. In addition, selection or screening can be carried out during a particular developmental stage in which the phenotype is exhibited by the plant.

A related embodiment provides methods to detect the presence of an allelic variant of Potri.002G146400 in a plant. The method involves selecting a plant having high or low sugar release, such as high or low glucose or xylose release, and determining the sequence of the gene at the Potri.002G146400 locus in said plant.

Inhibitors and Expression Vectors for Modulating the Activity of Potri.002G146400

Further disclosed herein are nucleic acid inhibitors of expression of Potri.002G146400, or inhibitors of expression of allelic variants of Potri.002G146400 including SEQ ID NO: 1, which can be used to reduce expression of the Potri.002G146400 gene and allelic variants thereof, to provide low lignin biosynthesis, high sugar release, and/or increased resistance to stress or pathogens. Specific nucleic acid inhibitors include antisense RNA, small interfering RNA, RNAi, microRNA, artificial microRNA, and ribozymes. Inhibitors of Potri.002G146400 activity include expression vectors encoding a Potri.002G146400 allelic variant with an increased number of glutamine repeats relative to the number of glutamine repeats in the sequence of SEQ ID NO: 2, operably linked to a regulatory region that is functional in a plant.

The polynucleotides and expression vectors described herein can be used to increase or inhibit expression of Potri.002G146400 or a Potri.002G146400 allelic variant. The term "expression" refers to the process of converting genetic information of a polynucleotide into RNA through transcription, which is catalyzed by an enzyme, RNA polymerase and into protein, through translation of mRNA on ribosomes. Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

A "nucleic acid inhibitor" is a nucleic acid that can reduce or prevent expression or activity of a target gene. For example, an inhibitor of expression of Potri.002G146400 can reduce or eliminate transcription and/or translation of the Potri.002G146400 gene product, thus reducing Potri.002G146400 protein expression.

An altered level of gene expression refers to a measurable or observable change in the level of expression of a transcript of a gene, or the amount of its corresponding polypeptide, relative to a control plant or plant cell under the same conditions (e.g., as measured through a suitable assay such as quantitative RT-PCR, a Northern blot, a Western blot or through an observable change in phenotype, chemical profile or metabolic profile). An altered level of gene expression can include up-regulated or down-regulated expression of a transcript of a gene or polypeptide relative to a control plant or plant cell under the same conditions. Altered expression levels can occur under different environmental or developmental conditions or in different locations than those exhibited by a plant or plant cell in its native state.

Techniques for introducing nucleic acids (inhibitors and expression vectors) into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863. If a cell or tissue culture is used as the recipient tissue for transformation, plants can be regenerated from transformed cultures if desired, by techniques known to those skilled in the art. See, e.g., Niu et al., *Plant Cell Rep.* V19:304-310 (2000); Chang and Yang, *Bot. Bull. Acad. Sin.*, V37:35-40 (1996) and Han et al., *Biotechnology in Agriculture and Forestry*, V44:291 (ed. by Y. P. S. Bajaj), Springer-Vernag, (1999).

Nucleic Acid Inhibitors

A number of nucleic acid based methods, including antisense RNA, ribozyme directed RNA cleavage, post-transcriptional gene silencing (PTGS), e.g., RNA interference (RNAi), microRNA and artificial microRNA and transcriptional gene silencing (TGS) can be used to inhibit Potri.002G146400 expression in plants. Suitable inhibitors include full-length nucleic acids of allelic variants of Potri.002G146400, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the antisense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., *PNAS* 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., Plant Physiol., 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, Antisense Nucleic Acid Drug Dev., 7:187-195; Hyrup et al., Bioorgan. Med. Chem., 4:5-23 (1996). In addition, the deoxyphosphate backbone can be replaced with, for example, a phosphorothioate or phosphorodithioate backbone, a phosphoroamidite or an alkyl phosphotriester backbone.

Expression Vector Modulators of Potri.002G146400 and Uses Thereof.

This disclosure provides methods of altering lignin synthesis and sugar release in a plant, comprising introducing into a plant cell an exogenous nucleic acid with a regulatory region operably linked to a nucleic acid encoding a Potri.002G146400 allelic variant, where a tissue of a plant produced from the plant cell has an altered cell wall compared to the cell wall in tissue of a control plant that does not comprise the nucleic acid.

In one embodiment, the exogenous nucleic acid is an expression vector encoding the polypeptide of a Potri.002G146400 allelic variant that leads to low, inhibited or decreased lignin synthesis. Expression of such a vector in a plant or plant cell would lead to a decrease in lignin synthesis in that plant or plant cell. This expression vector would be useful, for example, for increasing sugar release, that is, increasing glucose and/or xylose release, in a plant or plant cell in which the expression vector is introduced, relative to plants or plant cells which are not transformed by the vector. This expression vector would also be useful for decreasing lignification or lignin production in a plant or plant cell in which the expression vector is introduced.

In another embodiment, the exogenous nucleic acid is an expression vector encoding the polypeptide of a Potri.002G146400 allelic variant that leads to high or increased lignin synthesis. An example of such an expression vector is an expression vector comprising the Potri.002G146400 allelic variant encoding SEQ ID NO: 2. This expression vector would be useful, for example, for increasing lignin synthesis in a plant or plant cell in which the expression vector is introduced, relative to plants or plant cells which are not transformed by the vector.

Vectors containing nucleic acids such as those described herein are provided. A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci.* USA, 86:7890-7894 (1989)), root cell specific promoters reported by Conkling et al., *Plant Physiol.,* 93:1203-1211 (1990) and the tobacco RD2 promoter.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab IR promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis* SUC2 sucrose-H+ symporter promoter (Truernit et al., *Planta,* 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate:CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant*

Cell, 3(10):1051-1061 (1991)), the *Commelina* yellow mottle virus (CoYMV) promoter (Medberry et al., *Plant Cell*, 4(2):185-192 (1992)) and the rice tungro baciliform virus (RTBV) promoter (Dai et al., *Proc. Natl. Acad. Sci. USA*, 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

In one example, the coding sequence of a Potri.002G146400 allelic variant is amplified from either genomic DNA or cDNA by PCR. The DNA fragments are then subcloned into an expression construct. In this example, a construct is made by first digesting pSAT4A-DEST-n(1-174)EYFP-N1 (ABRC stock #CD3-1080) and pSAT5-DEST-c(175-end)EYFP-C1(B) (ABRC stock #CD3-1097) (Citovsky V. et al., *J Mol Biol* 362:1120-1131 (2006)) with NdeI and BglII, then ligating the 1.1 kb fragment of the first construct and 4.4 kb fragment of the second one, followed by subcloning of the coding sequence of a Potri.002G146400 allelic variant into the construct to create the expression vector.

Transgenic Plants/Plant Species/Plant Cells

Also disclosed herein are plants and plant cells genetically modified by introduction of the disclosed inhibitors and expression vectors. In certain cases, a transgenic plant cell or plant comprises at least two recombinant nucleic acid constructs or exogenous nucleic acids, e.g., one including a nucleic acid encoding a Potri.002G146400 allelic variant or homolog, and another including a nucleic acid encoding a second Potri.002G146400 allelic variant or one or more different cell wall modulating polypeptides.

A plant or plant cell used in methods of the invention contains a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days or about 1-3 days. The use of transient assays is particularly convenient for rapid analysis in different species or to confirm expression of a heterologous Potri.002G146400 allelic variant whose expression has not previously been confirmed in particular recipient cells.

Initial and immediate application of the expression of Potri.002G146400 allelic variants can be made in the bioenergy crops *Populus* and switchgrass, but the application can be extended to other bioenergy crops such as corn, other sources of lignocellulosic biomass and other model plants e.g., *Salix, Miscanthus*, rice and *Medicago*.

For example, the polynucleotides and vectors described herein can be used to transform a number of monocotyledonous and dicotyledonous plants and plant cell systems, including alfalfa, ash, beech, birch, canola, cherry, clover, cotton, cottonseed, eucalyptus, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, *miscanthus*, oat, rice, rye, ryegrass, *sorghum*, sudangrass, sugarcane, sweet corn, switchgrass, turf grasses, timothy and wheat. Gymnosperms such as fir, pine and spruce can also be suitable.

The methods and compositions can be used over a broad range of plant species, including species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus, oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea, Miscanthus* hybrid (*Miscanthus×giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

In one aspect, a plant cell is provided. The plant cell comprises an endogenous or exogenous nucleic acid comprising a regulatory region operably linked to a polynucleotide encoding a Potri.002G146400 allelic variant where a tissue of a plant produced from the plant cell has an altered cell wall compared to the cell wall in tissue of a control plant that does not comprise the nucleic acid.

The cell can further comprise a nucleic acid encoding a second Potri.002G146400 allelic variant operably linked to a second regulatory region. The nucleic acid encoding a second Potri.002G146400 allelic variant operably linked to a second regulatory region can be present on a second recombinant nucleic acid construct. This allows expression of the Potri.002G146400 allelic variant in multiple combinations, such as under control of different promoters or multiple copies of the gene.

In another aspect, a plant cell comprising a Potri.002G146400 nucleic acid inhibitor is provided. The plant cell comprises an exogenous nucleic acid, the exogenous nucleic acid comprising a regulatory region operably linked to a polynucleotide that is transcribed into an interfering RNA effective for inhibiting expression of Potri.002G146400 or a Potri.002G146400 allelic variant. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

In another aspect, a plant is provided. The plant comprises any of the plant cells described above. Progeny of the plant also are provided, where the progeny have altered (increased or decreased) lignin synthesis.

Methods of Use of Transgenic Plants

Disclosed herein are methods to increase glucose and/or xylose release in a plant or plant cell, or to decrease lignin synthesis, by expressing the disclosed inhibitors, or expressing expression vectors encoding a Potri.002G146400 allelic variant that leads to reduced lignin synthesis, in plants and plant cells.

Further disclosed herein are improved methods of producing biofuel from cellulosic biomass, by using plants with reduced or inhibited expression or activity of the Potri.002G146400 gene in biofuel production processes. Methods of pretreatment and saccharification of biomass to fermentable sugars, followed by fermentation of the sugars to ethanol, are known in the art.

Additionally disclosed are methods for increasing lignin synthesis in a plant or plant cell, by expressing expression vectors encoding a Potri.002G146400 allelic variant that leads to increased lignin synthesis (for example, an expression vector encoding SEQ ID NO: 2), in a plant or plant cell of interest. Additionally disclosed are methods of producing paper and pulp, by using plants with increased expression of the Potri.002G146400 gene in paper or pulp production processes, as known in the art.

Articles of Manufacture

The materials and methods described herein are useful for modifying biomass characteristics, such as characteristics of biomass renewable energy source plants. "Biomass" refers to any cellulosic or lignocellulosic raw material and includes materials containing cellulose, and optionally further containing hemicellulose, lignin, starch, oligosaccharides and/or monosaccharides. The term "cellulosic" refers to a composition containing cellulose. The term "lignocellulosic" refers to a composition containing both lignin and cellulose. According to the invention, biomass may be derived from a single source, or biomass can contain a mixture derived from more than one source; for example, biomass can contain a mixture of corn cobs and corn stover, or a mixture of grass and leaves. Examples of biomass include, but are not limited to, tree crops such as *Populus*, corn grain, corn cobs, crop residues such as corn husks, corn stover, grasses, wheat, wheat straw, barley, barley straw, hay, rice straw, switchgrass, waste paper, sugar cane bagasse, *sorghum*, soy, components obtained from processing of grains, trees, branches, roots, leaves, wood chips, sawdust, shrubs and bushes, vegetables, and fruits.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

The invention also relates to the use of the pulp obtained from the disclosed genetically modified plants in the production of cellulose-based products, for example, in the paper industry, or for the production of cardboard. Pulp, produced using plants which have been genetically modified to have increased expression of the Potri.002G146400 gene and therefore also have increased lignin synthesis, can be used as a building material and in particular as output material for pressed chipboard, fiberboard of medium density, or as filler material.

Seeds of transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material or a label inserted within the package. The package label may indicate that the seed herein incorporates transgenes that provide increased amounts of lignin or altered S/G lignin ratio in one or more tissues of plants grown from such seeds.

The present disclosure is further illustrated by the following non-limiting examples.

EXAMPLES

Figure 3:
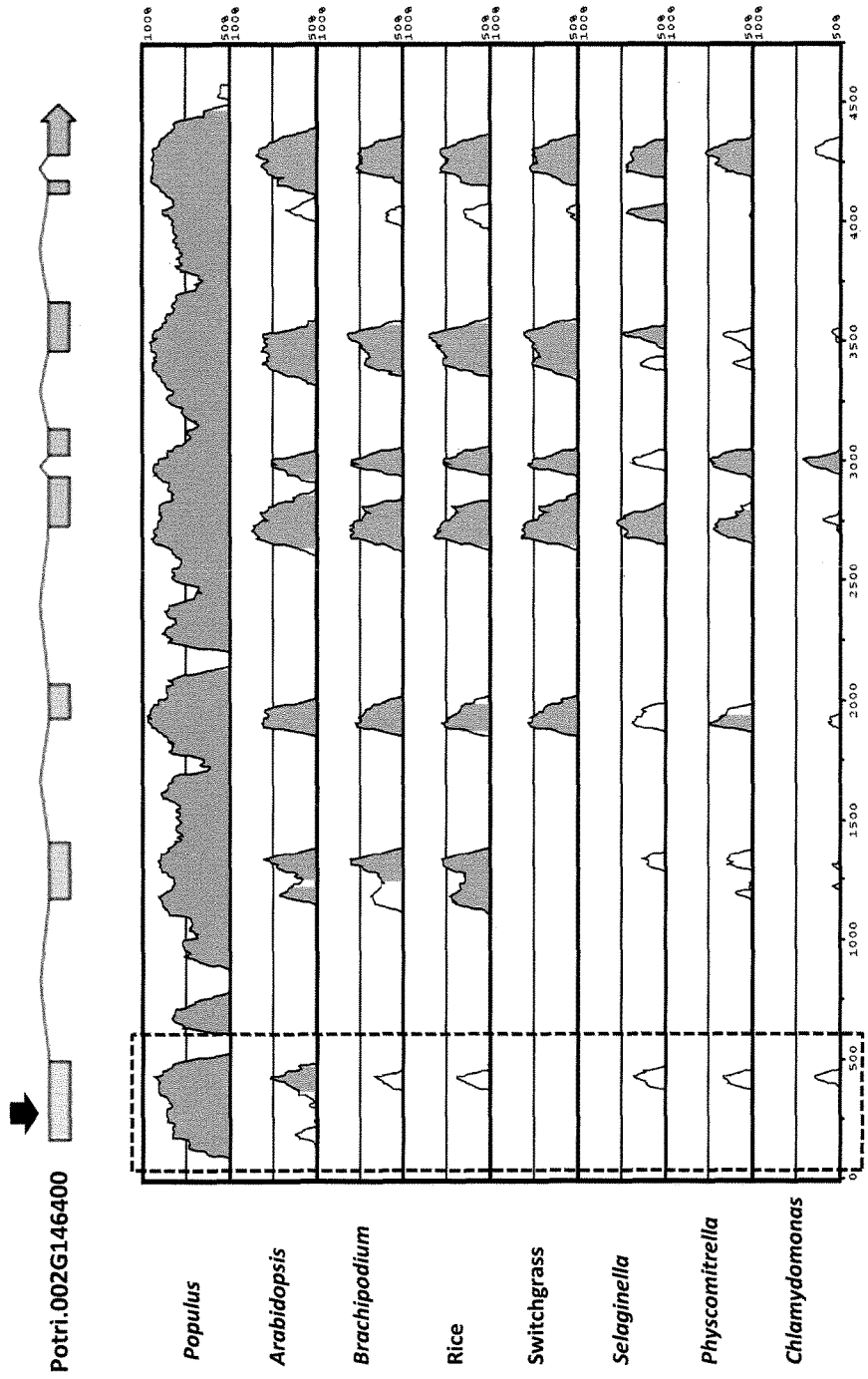
FIG. 3. Vista alignments showing levels of genomic sequence conservations between *Populus* Potri.002G146400 and *Populus* paralog Potri.014G068300, *Arabidopsis* ortholog, representative mocot orthologs and non-vascular plants orthologs.
Figure 4A:
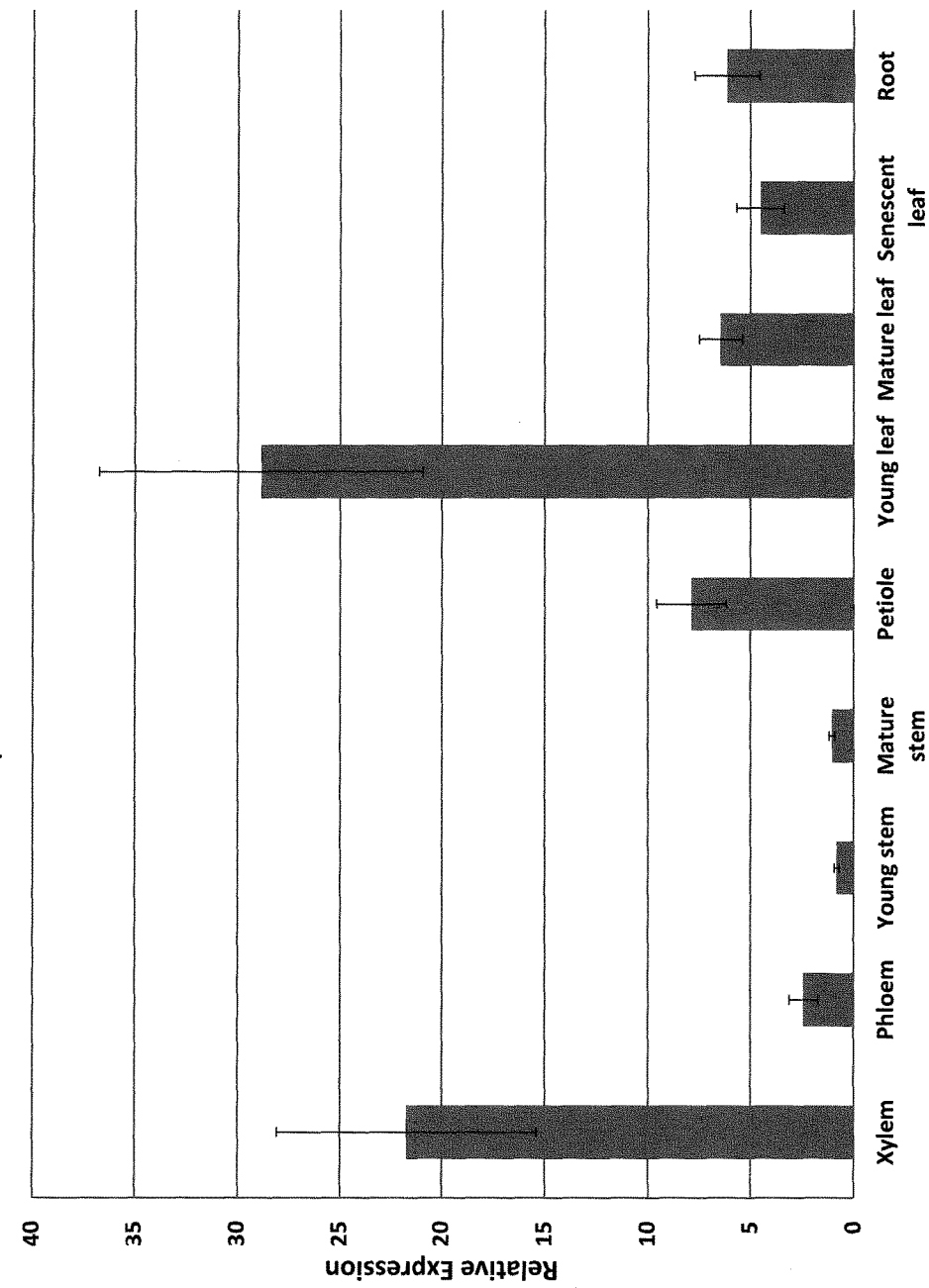
FIG. 4A. Expression analysis for Potri.002G146400 across tissue types.
Figure 4B:
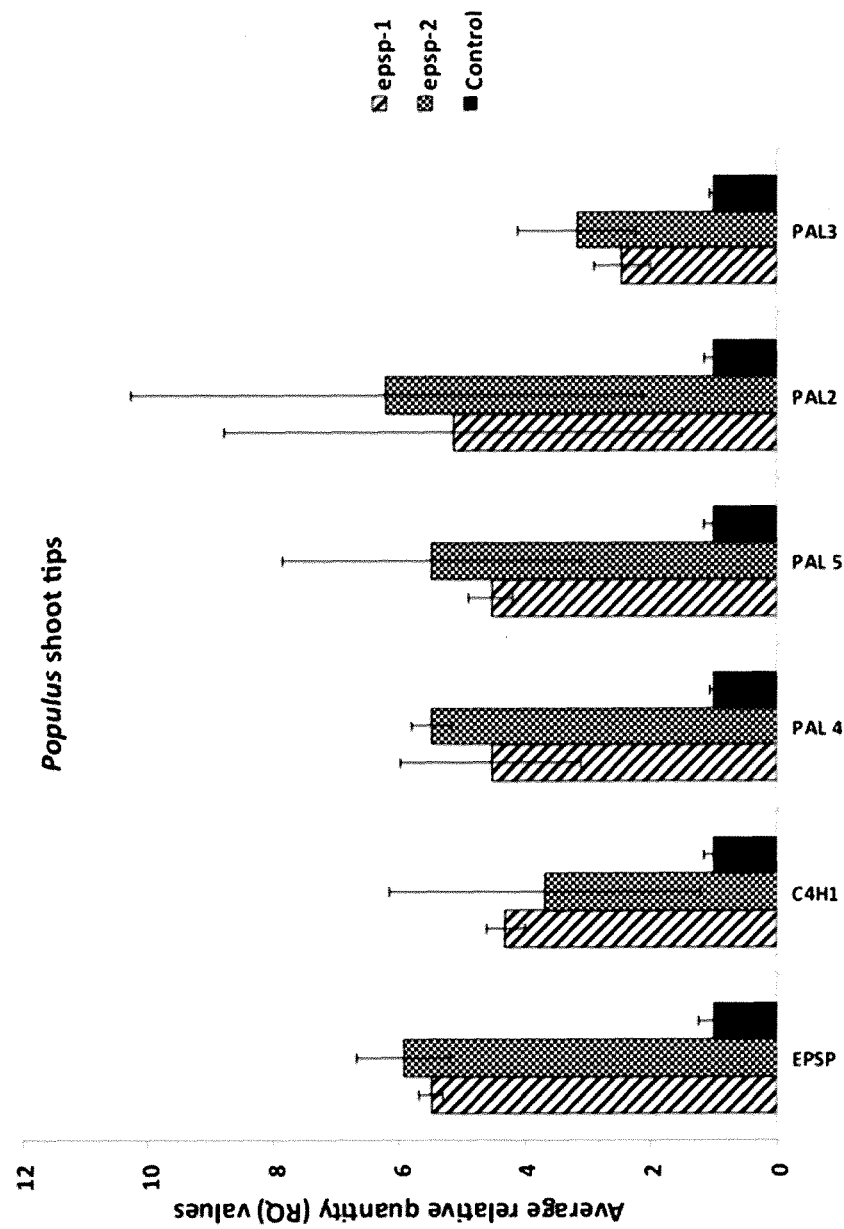
FIG. 4B. Transcriptional response of Phenylalanine Ammonia Lyase (PAL) and Cinnamate 4-Hydroxylase (C4H1) genes in overexpression transgenic lines EPSP-OX1 and EPSP-OX2.

The HTH motif is not found in the presumed prokaryotic progenitor of the enzyme. We assessed penetrance of the motif in plants by surveying 57 EPSP isofoiius derived from 42 sequenced plant genomes available in the Phytozome database (www.phytozome.net). Phylogenetic relatedness of sequences closely mirrored broader classification delineating monocot, dicot, non-vascular and algae clades of the kingdom plantae. The most striking feature based on this survey was that the exon encoding putative HTH motif is highly divergent between dicots and monocots, mosses and algae (FIG. 3). Sequence alignments suggests that, unlike other plants, dicots share a start codon and a motif of conserved MAQV(A/L/I)S(T) (SEQ. ID. NO: 3) amino acid residues further upstream from ancestral EPSP start site. Although the *Populus* Potri.014G068300 utilizes the downstream start position which produces an ancestral isoform, analysis of genomic sequence revealed high levels of conservation and the presence of an ATG codon at the same position as the HTH-harboring paralog Potri.002G146400, suggesting that the HTH motif at Potri.014G068300 may have been lost after the Salicoid whole-genome duplication event (FIG. 3). In fact, Potri.014G068300 was a pseudogene based on an apparent frameshift mutation in the first exon of the longer transcript. qPCR expression profiling across tissue-types suggested that transcripts for the HTH-harboring isoform was highly abundant in young leaf, although it was also detected across tissue types (FIG. 4A). RNAseq data from Bao et al. (*BMC Genomics*, 14:359, 2014) also showed that Potri.002G146400 transcript levels were 100× greater than the Potri.0014G68300 paralog in developing xylem sampled from 20 different *P. trichocarpa* genotypes.

Taken together, 1) the presence of an HTH motif typically associated with transcriptional regulation via DNA or RNA binding, 2) the apparent uniqueness of the isoform to dicots and 3) its high expression levels in the chloroplast-devoid xylem tissue, provided the impetus for transgenic evaluation of the isoform to assess novel functions.

To evaluate transcriptional response of phenylpropanoid genes, we generated transgenic lines in the *Populus deltoides* WV94 background over-expressing the HTH-harboring isoform and performed targeted qPCR as well as RNAseq analyses to assess transcriptional responses. Overexpression of the target isoform was confirmed in young shoots using two independent transgenic events, EPSP-OX1 and EPSP-OX2. Targeted qPCR was performed to assay expression-levels of four PAL paralogs (Potri.00G126800, Potri.008G038200, Potri.010G224100 and Potri.016G091100) and a C4H1 gene (Potri.019G130700). All five target-genes exhibited significantly increased expression in young shoot tips of overexpression lines compared to the empty vector control. The observed increase in PAL and C4H1 expression in response to overexpression of the EPSP HTH-isoform strongly implies a novel transcriptional regulatory function targeting the phenylpropanoid pathway in *Populus*. Since the transcriptional regulation of the phenylpropanoid pathway and secondary cell wall biosynthesis has been extensively studied yielding a core set of transcription factors that are conserved across multiple species, we sought to determine the position of the EPSP HTH-isoform in this established transcriptional hierarchy. To that end, we evaluated the transcriptional response of this isoform to overexpression of the Secondary wall-associated NAC Domain (SND1) transcription factor. Since SND1 has been shown to be the master regulator of secondary cell wall biosynthesis, the novel isoform would be expected to fall under the control of this transcription factor. Additionally, we evaluated global transcriptional changes in EPSP-OX1 line using RNAseq analysis to characterize putative downstream targets of the novel transcription regulator.

Figure 4C:
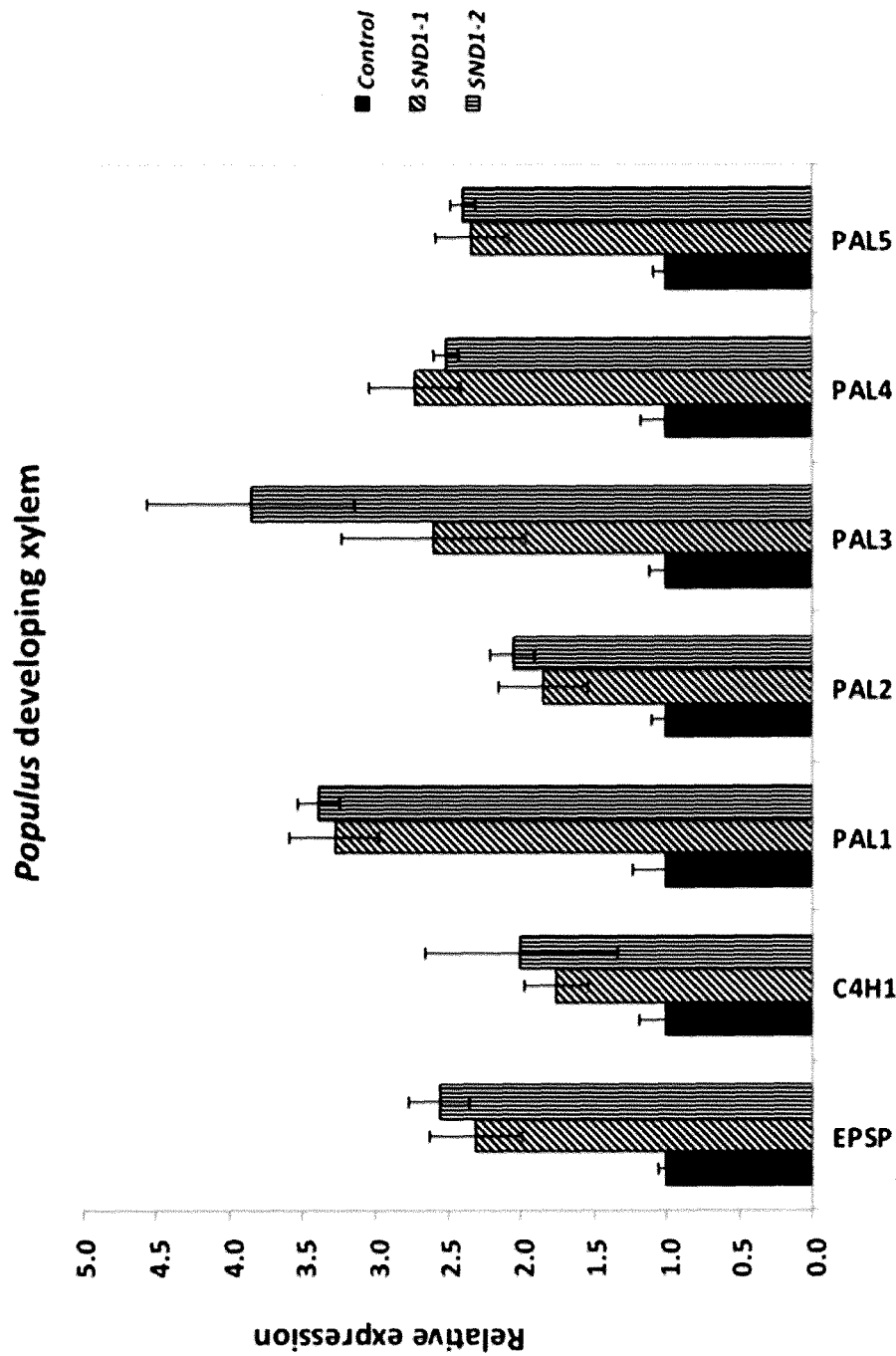
FIG. 4C. Transcriptional response of the EPSP Potri.002G146400 paralog and downstream targets PAL and C4H1 to overexpression of the Secondary cell wall NAC domain transcription factor (SND1).

The EPSP HTH-isoform exhibited significantly increased expression in two independent SND1 overexpression lines relative to the control (FIG. 4C). As expected, downstream targets C4H1 and PALs were also upregulated in the SND1 overexpression lines. Based on differential gene expression analysis, 68 genes were significantly upregulated in the over-expression lines relative to the empty-vector controls. On the other hand, 18 genes were significantly downregulated. Most importantly, genes encoding two secondary master switches for secondary wall transcriptional regulation, NAC Secondary Wall Thickening Promoting Factor 1 (NST1) and MYB46, exhibited 2.2- and 2.5-fold increases in expression, respectively. Since specific roles for these three transcription factors have been firmly established they provide important anchors for the placement of the EPSP transcription factor in the context of transcriptional regulation of secondary cell wall biosynthesis. These data suggested that the EPSP HTH-isoform functions down-stream of SND1 but upstream of NST1 and MYB46 and is likely a, hitherto, uncharacterized transcriptional master switch. In support of this role, we observed that an ortholog of the *Arabidopsis* subunit of the transcriptional coregulatory complex Mediator complex (REF4-related 1) exhibited a 1.3-fold increase in expression. Studies suggested that REF4-related 1 is a key regulator in maintenance of phenylpropanoid homeostasis in *Arabidopsis*. Coexpression analysis of the *Populus* REF4-related 1, Potri.008G201600, revealed a strong correlation in expression (r≥0.99) with lignin pathway genes cinnamyl-alcohol dehydrogenase (CAD), 4-coumarate-CoA ligase (4CL) and caffeic acid O-methyltransferase (COMT). Outside of transcriptional regulators, genes with well-documented functions in the phenylpropanoid pathway and secondary cell wall formation were also significantly upregulated in the EPSP-OX1 overexpression line, including Laccases (LAC), Irregular Xylem 7 and 8 (IRX7-8), Trichome Birefringence-Like genes (TBLs), Reduced Wall Acetylation (RWA) and Tubulin Alpha-5 (TUA5).

Based on the putative transcriptional regulatory functions described above, we hypothesized that this EPSP isoform should localize outside of the chloroplast in order to perform regulatory functions. To evaluate this, we used a *Populus* protoplast transient expression system to assess subcellular localization of the isoform fused with an N-terminal GFP signal. The GFP signal localized in the nucleus and could not be detected in chloroplasts. Additionally, sequence analysis revealed a KKLK (SEQ. ID. NO: 4) nuclear localization signal at amino acid positions 144-147 of the regulatory isoform. As such, these cumulative results provide additional support for the novel function proposed here.

Changes in gene expression also extended into the flavonoid pathway which occurs downstream of phenylpropanoid biosynthesis in plants. The well-documented positive regulator of anthocyanin biosynthesis, COP 1-interacting protein 7 (CIP7) exhibited a 99% increase in expression in the overexpression transgenic lines. Yamamoto et al. (*The Plant Cell,* 10:1083-1094, 1998) demonstrated that antisense transgenic plants targeting CIP7 had reduced expression of genes involved in anthocyanin biosynthesis. This apparent induction of the flavonoid pathway was corroborated by GC-MS-based metabolomic analysis that revealed up to 3-fold increase in levels of flavonoids such as quercetins, dihydromyricetin and catechins in the two overexpression lines. Lignin pathway metabolites feruloyl glycoside, ferulic acid, caffeoyl conjugates and phenolic compounds showed increases between 7 and 87% in the over-expression lines.

Additionally, assessment of cell wall phenotypes using quantitative saccharification revealed significant reduction in xylose content in the two lines. Reductions were 5.8% and 11.8% for EPSP-OX1 and EPSP-OX2, respectively. A lesser but opposite trend was observed for glucose content, which exhibited slight increases of 1.3 and 6.2 for EPSP-OX1 and EPSP-OX2, respectively. Pyrolysis Molecular Beam Mass Spectrometry (pyMBMS) analysis revealed insignificant changes in percent lignin content, with the two lines ranging from 21.4-23.2% for EPSP-OX1 and EPSP-OX2 respectively, compared to 23.3% for the control. There were no significant differences in syringyl-to-guaiacyl ratio (S/G) between the transgenics and controls. To assess the impact of these cumulative changes on cell wall recalcitrance, we measured saccharification efficiency using separate hydrolysis and fermentation (SHF). Both overexpression lines exhibited improved saccharification for both glucose and xylose after normalizing for the amount of starting cellulose and xylan, respectively. Xylose yield increases ranged from 22.4 to 56.7%, whereas glucose yield increases ranged from 6.1 to 39.3% across two different experiments for EPSP-OX1 and EPSP-OX2, respectively.

In conclusion, we provided multiple lines of evidence suggesting that a *Populus* EPSP synthase acquired novel transcriptional regulatory function and is a putative master switch for genes in the phenylpropanoid and flavonoid pathways. It is therefore intriguing, that this shikimate pathway derived-EPSP HTH-isoform evolved a regulatory function modulating expression of processes that are coincidentally specialized in dicots relative to other plants. The presence of an apparently conserved start position upstream of the sequence encoding the native EPSP isoform in dicots may point to the existence of an ancestral HTH motif that underwent subsequent divergence in dicots and was possibly lost entirely in the progenitor of modern day monocots in the same manner that it was lost of one of the *Populus* paralog.

What is claimed is:

1. A method for increasing glucose and/or xylose release in a plant or plant cell, comprising overexpressing an exogenous nucleic acid encoding an Potri.002G 146400 allelic variant comprising SEQ ID NO:2 in said plant or plant cell.

2. A method for increasing phenylalanine, tyrosine, tryptophan and flavonoid production in a plant or plant cell, comprising overexpressing an exogenous nucleic acid encoding an Potri.002G 146400 allelic variant comprising SEQ ID NO:2 in said plant or plant cell.

3. A plant or plant cell genetically modified by introduction of an expression vector comprising a nucleic acid encoding an exogenous Potri.002G 146400 allelic variant comprising SEQ ID NO:2.

* * * * *